(12) United States Patent
Leppelmeier

(10) Patent No.: US 6,312,432 B1
(45) Date of Patent: Nov. 6, 2001

(54) BONE DRILL

(75) Inventor: John W. Leppelmeier, Bryan, OH (US)

(73) Assignee: Nemco Medical, Inc., Hicksville, OH (US)

( * ) Notice: Subject to any disclaimer, the term of this patent is extended or adjusted under 35 U.S.C. 154(b) by 0 days.

(21) Appl. No.: 09/686,566

(22) Filed: Oct. 11, 2000

Related U.S. Application Data
(60) Provisional application No. 60/186,492, filed on Mar. 2, 2000.

(51) Int. Cl.⁷ .................................................. A61B 17/16
(52) U.S. Cl. ............................ 606/80; 408/225; 408/228; 408/230
(58) Field of Search ............................... 606/80, 96, 180; D15/139; 433/165; 408/225, 227, 228, 229, 230, 704, 210

(56) References Cited

U.S. PATENT DOCUMENTS

| 3,779,664 | * | 12/1973 | Caley et al. ..................... 408/225 |
| 4,330,229 | * | 5/1982 | Croydon ........................... 408/230 |
| 4,968,193 | | 11/1990 | Chaconas et al. . |
| 5,055,105 | | 10/1991 | Hamlin et al. . |
| 5,346,496 | | 9/1994 | Pennig . |
| 5,634,927 | | 6/1997 | Houston et al. . |
| 5,649,930 | | 7/1997 | Kertzner . |
| 5,685,673 | * | 11/1997 | Jarvis ............................... 408/230 |
| 5,741,267 | * | 4/1998 | Jorneus et al. .................... 606/80 |
| 5,766,179 | | 6/1998 | Faccioli et al. . |
| 5,769,856 | | 6/1998 | Dong et al. . |
| 5,791,902 | | 8/1998 | Lauks . |
| 5,833,691 | | 11/1998 | Bimman . |
| 5,928,238 | | 7/1999 | Scarborough et al. . |

OTHER PUBLICATIONS

Brochure of Mohawk Tools, Inc. for "Mohawk Cutting Tools" dated Jun. 1981.
A.S.T.E. Handbook entitled "Tool Engineers Handbook" published 1949.

* cited by examiner

Primary Examiner—David O. Reip
Assistant Examiner—Julian W. Woo
(74) Attorney, Agent, or Firm—Emch, Schaffer, Schaub & Porcello, Co., L.P.A.

(57) ABSTRACT

A bone drill extending along an axis has (1) a stabilizing point with first and second cutting edges which extend to a tip, conical wall sections and flutes on opposite sides of each of the first and second cutting edges and (2) first and second lands extending radially outwardly from the conical wall sections, each land having a radially outwardly extending cutting edge.

25 Claims, 3 Drawing Sheets

BONE DRILL

RELATED APPLICATION

The present application claims priority to U.S. Provisional Patent Application Ser. No. 60/186,492 filed Mar. 2, 2000.

BACKGROUND OF THE PRESENT INVENTION

The present invention relates to a drill specifically designed for drilling cavities or apertures in bones during the performance of surgical procedures.

In performing surgical procedures involving the repair of bones, the setting of broken bones or the replacement of joints, it is frequently necessary to drill cavities or apertures suitable for receiving bone screws. For example, in the case of fractures, the screws may be utilized for securing bone plates for fixation of the fractured sections. Screws may also be used in a variety of joint replacements and compression hip plates among other applications.

Prior art drills for use in bone surgery are difficult to precisely position during the drilling process. The prior art drills are derivative of metal cutting drills and have a tendency, at the beginning of the drilling operation, to move slightly from the desired axis of the aperture being drilled. This difficulty is particularly pronounced when the surgeon is attempting to start the drilling process on a portion of the bone which has a non-flat surface. Prior art bone drills have points which are not self-retaining on the desired axis. This is particularly true for drills for forming apertures having a diameter greater than about 1/8 41.

Additionally, the prior art bone drills have tips which do not immediately start the cutting operation when the tip contacts the bone surface. In order to overcome the problem with respect to accurate positioning of the prior art drills, the surgeons were forced to either (1) using a bushing to guide the drill, (2) use a relatively smaller drill as a starter and use the desired diameter drill in a subsequent operation or (3) attempt to start the drilling at a flat part of the bone, at an oblique angle to the desired axis of the cavity or aperture, and then straighten the drill to the desired axis. None of these solutions is particularly satisfactory and frequently result in the cavity or aperture being drilled having an irregular, non-cylindrical surface. This can lead to premature loosening of the screws. The prior art drills, when used with drill guides, result in excessive wear between the drill and drill guide causing wear debris to be generated which can lead to bone necrosis or infection which could lead to loosening of the screws. The other prior art procedures using prior art bone drills can also result in excessive bone debris being generated which can rapidly fill the flutes leading to generation of excessive heat and more bone necrosis.

Under the present invention, there is provided a drill which can be used in a one-step drilling operation with precise positioning and immediate retention along the desired axis upon contact of the tip with the bone. The drill of the present invention has a stabilizing point having tapered cutting edges with adjacent flutes. The tapered cutting edges extend to the tip and begin the cutting action immediately upon contact of the stabilizing point with the bone. Spaced axially from the tip of the stabilizing point are spaced apart cutting edges lying on a plane perpendicular to the axis of the drill which are arcuately displaced from one another approximately 180°. These spaced apart cutting edges follow a straight line path and, after the start, cooperate with the stabilizing point (a) to prevent the drill from "walking" or moving off the desired axis, (b) to assure that the cavity being cut is round or cylindrical even if the aperture is being cut at an oblique angle on a circular surface and (c) to prevent packing of bone chips by causing the chips to be readily expelled from the site being drilled. The drill of the present invention permits the drilling of an aperture or cavity in the bone in a one-step operation even though the origin of the drilling is a non-flat bone surface. It has a fluted design which permits bone chips to be augured away from the bone interface with the result that less heat is transferred to the bone interface than with prior art drills thus lessening bone necrosis.

The present invention is also directed to a method for forming an aperture or cavity in a bone.

IN THE DRAWINGS

DETAILED DESCRIPTION OF THE INVENTION

Figure 1:
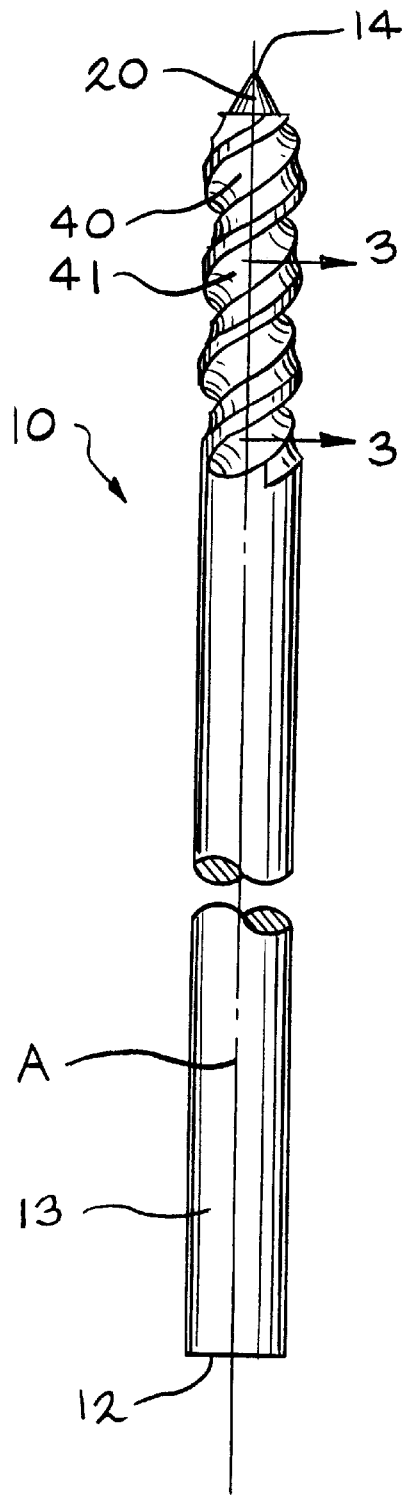
FIG. 1 is an elevational view showing the drill of the present invention.

Referring to the drawings, there is shown a drill generally designated by the numeral 10 extending along an axis A from a first free end 12 of a shank 13 intended to be engaged to a power source such as a drill to a second end 14 defining the tip of a stabilizing point 20. Spaced axially from the second end 14 defining the tip are two spaced apart cleared lands 22 and 23 disposed substantially perpendicular to the axis A. The leading portion of each cleared land 22, 23, as the drill rotates in a counterclockwise direction as viewed in FIG. 2 (as shown by the arrow), defines a cutting edge 24, 25. The cutting edges 24, 25 are disposed on a plane perpendicular to the axis A and at an angle of approximately 180° relative to one another. The drill 10 is preferably a right hand helix, right hand cutting tool.

The stabilizing point 20 is provided a pair of angled cutting edges 31, 32, each of which has a flute forwardly thereof, namely, a flute 33 for cutting edge 31 and a flute 34 for cutting edge 32. The angled cutting edges 31, 32 meet at the second end 14 in a very sharp point. The angled cutting edges 31, 32 and their respective flutes 33, 34 ensure that the stabilizing point 20 will immediately begin cutting bone as soon as the second end 14 contacts the bone. The sharpness of the tip defined at the second end 14 coupled with the feature of the angled cutting edges 31, 32 and their respective flutes 33, 34 ensures that the drill will form the aperture or cavity at the precise location of initial contact of the bone by the tip defined by the second end 14 irrespective of whether that portion of the bone being contacted has a flat or non-flat surface. The maintenance of the drill at precisely the location initially contacted by the second end 14 permits the surgeon to form the desired aperture or cavity in the bone while maintaining the drill 10 precisely along the axis at which the drill was positioned at the time of initial contact between the second end 14 and the bone.

Figure 2:
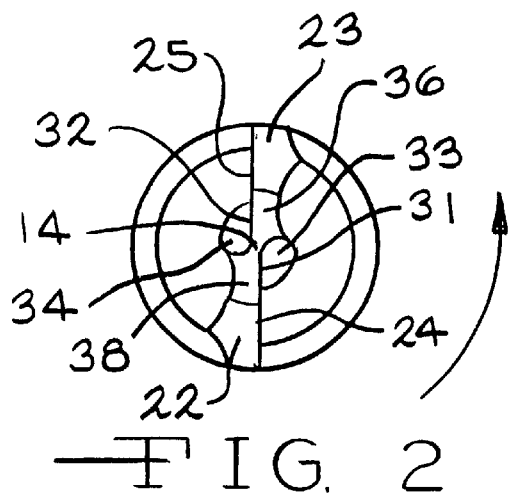
FIG. 2 is an end view of the drill.
Figure 4:
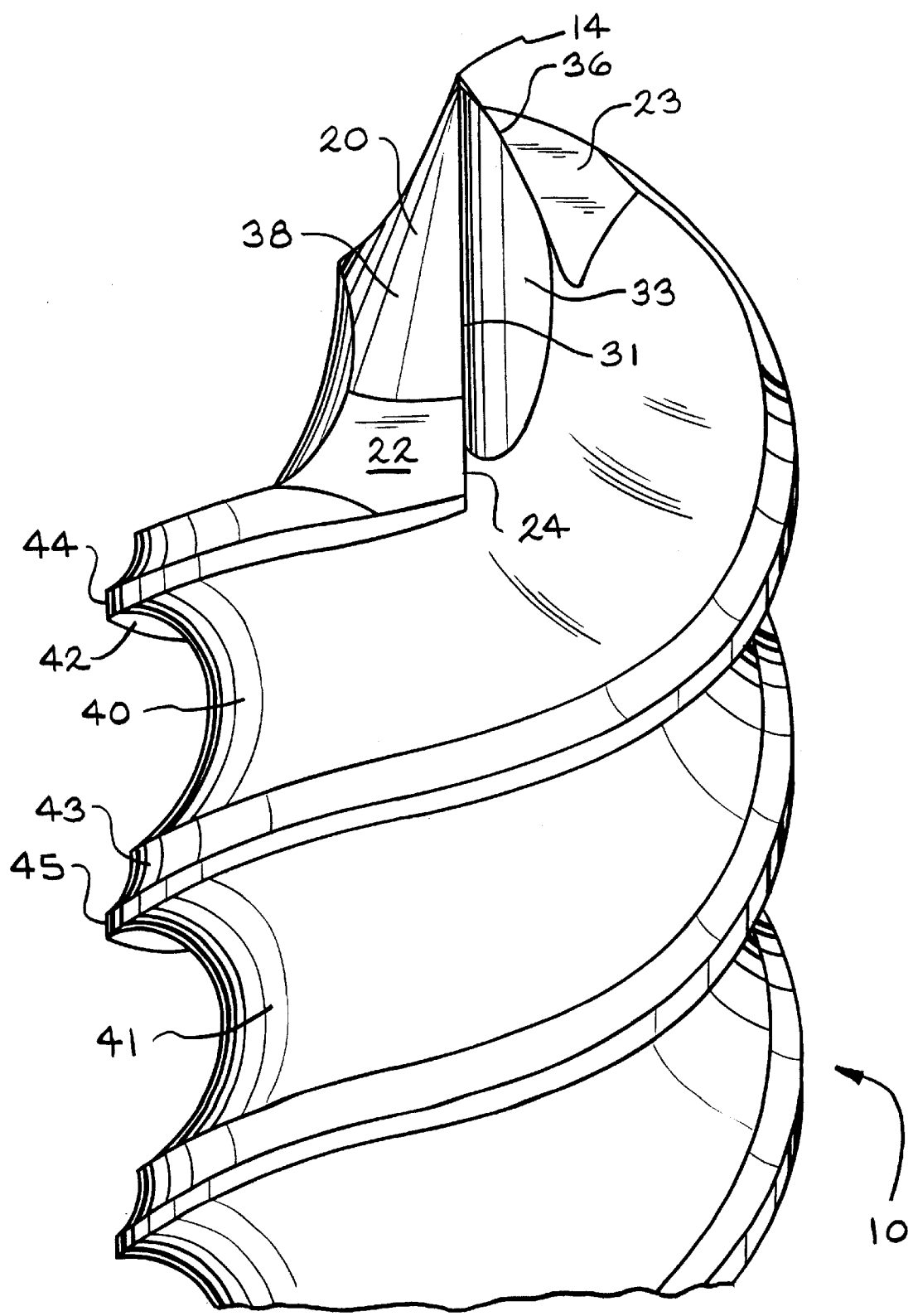
FIG. 4 is an enlarged perspective view of the end portion showing the stabilizing point and cutting edge immediately adjacent thereto.
Figure 5:
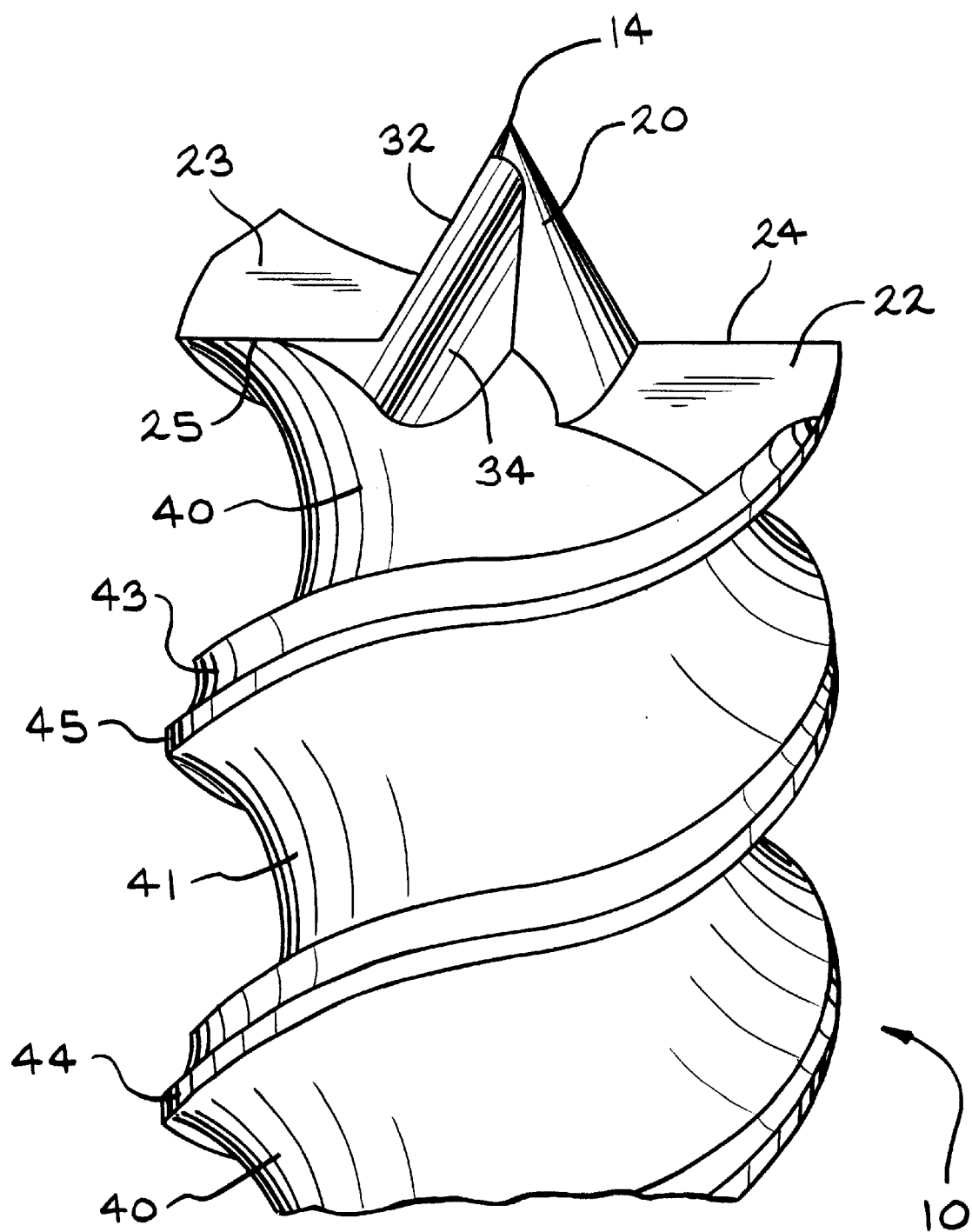
FIG. 5 is a view similar to FIG. 4 but with the drill rotated approximately 90°.

As may be seen in FIGS. 2 and 4, cutting edges 24 and 31 lie on substantially the same plane, which plane is parallel to the axis A. Similarly, the cutting edges 25 and 32 lie on substantially the same plane parallel to axis A. As can be seen in FIG. 2, plane of cutting edges 24 and 31 is slightly offset from the plane of cutting edges 25, 32; however, it is within the contemplation of this invention that all four of the cutting edges 24, 25, 31 and 32 could lie on the same plane.

The stabilizing point 20, in the area between the flutes 33 and 34, defines a pair of spaced apart wall surfaces 36, 38, each of which forms a section of a cone. As viewed in profile, the wall surfaces 36, 38 define an included angle of 60°±30°; however, best results are obtained when the included angle is 60°±10°. As will be appreciated, the greater the angle, the less stabilization which is provided upon contact of the bone by the tip of the second end 14; however, such greater angle will provide greater strength to the stabilizing point. Conversely, the smaller the angle, the greater will be the stabilization but with less strength.

Figure 3:
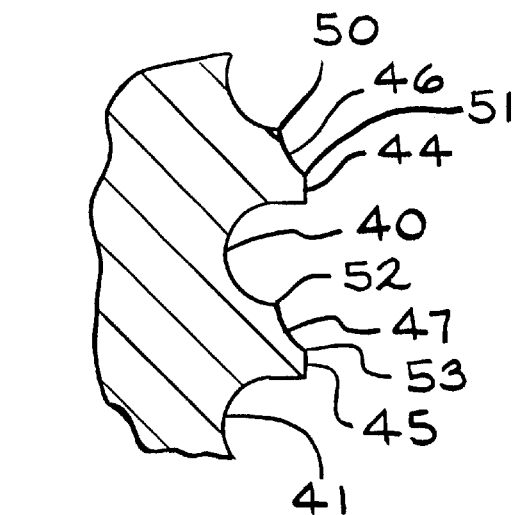
FIG. 3 is a sectional view taken through line 3—3 of FIG. 1.

Extending from each cutting edge 24, 25 is a helical flute 40, 41. Each turn of each helical flute 40, 41 is separated by a helical land or helical thread 42, 43, hereinafter referred to as "helical thread". As may be seen in cross-section in FIG. 3, each helical thread 42, 43 has a first cylindrical wall section 44 or 45 which is parallel to the axis A and a curved wall surface portion 46, 47. Each curved wall surface portion 46, 47, in section as viewed in FIG. 3, extends between end points, 50, 51 for curved surface portion 46 and end points 52, 53 for curved surface portion 47. A line extending between end points 50, 51 is disposed at an angle of approximately 30°±10° relative to the axis A. Similarly, a line extending between end points 52, 53 is disposed at an angle of approximately 30°±10° relative to the axis A.

The presence of the stabilizing point 20 and its angled cutting edges 31, 32 which commence cutting immediately upon penetration of the bone by the tip at the second end 14 coupled with the cutting edges 24, 25 being disposed on a plane perpendicular to the axis A along with the design of the helical flutes 40, 41 and helical threads 42, 43 with their cylindrical wall surface portions 44, 45 and curved wall surface portions 46, 47 cooperate to prevent the drill from walking thereby maintaining the drill 10 precisely on the desired axis A. This assures that the cavity being cut has a circular cross-sectional configuration even if it is being cut on an irregular surface or being cut at an oblique angle of the circular or rounded surface, as on a patella.

Additionally, the orientation of the flutes 33, 34 of the stabilizing point 20 causes the chips generated by its angled cutting edges 31, 32 to flow in one direction, for example, at an angle of approximately 30° to the axis A. In contrast, the direction of flow of the bone chips caused by the cutting edges 24, 25 is substantially parallel to the axis A as a result of directing the chips into the helical flutes 40, 41. The action of causing the chips to flow in two directions ensures that the chips are expelled from the drill 10 thereby preventing packing of bone chips which frequently occurs with prior art drills. This further prevents the build-up of undesirable heat which causes bone necrosis with subsequent loosening of screws. A larger surface area in the flutes than is available with prior art bone drills permits the bone chips exit faster than is possible with prior art bone drills. The larger surface area of the flutes also is a factor in minimizing build-up of heat.

The helix angle of the helical flutes 40,41 is preferably on the order of 60°; however, anything greater than 45° relative to the axis A is satisfactory.

The drill of the present invention can manufactured of any durable metal which is biocompatible.

In using the drill of the present invention, the surgeon may simply cut the soft tissue overlying the bone and proceed directly to drilling the bone along the desired axis without the necessity of (1) first drilling a small pilot hole or (2) starting the drilling at an angle oblique to the desired axis of the aperture. The bone, having no pilot hole or initial drilling at an oblique angle, may be considered as having a "virgin surface" in the area of drilling, in other words, a surface as appears immediately upon cutting the overlying soft tissue. It is not necessary to use a bushing to guide the drill; however, the surgeon may use one if he so desires.

Many modifications will be readily apparent to those skilled in the art.

I claim:

1. A bone drill comprising:
   (a) a shank extending along an axis from a first end toward a second end;
   (b) a stabilizing point extending to a tip at said second end, said stabilizing point including
      (i) first and second cutting edges extending to said tip, each said first and second cutting edge lying on a plane substantially parallel to said axis,
      (ii) a first flute adjacent said first cutting edge and a second flute adjacent said second cutting edge, and
      (iii) a substantially conical first wall section on the opposite side of said first cutting edge from said first flute and a substantially conical second wall section on the opposite side of said second cutting edge from said second flute; and
   (c) a first land extending outwardly from said first wall section, said first land including a first radially outwardly extending cutting edge and a second land extending outwardly from said second wall section, said second land including a second radially outwardly extending cutting edge.

2. A bone drill according to claim 1 wherein said first substantially conical wall section cooperates with said second substantially conical wall section to define an angle in the range of 60°±10°.

3. A bone drill according to claim 1 wherein said first land and said second land are substantially perpendicular to said axis.

4. A bone drill according to claim 1 wherein said first cutting edge and said first radially outwardly extending cutting edge lie on the same plane and said second cutting edge and said second radially outwardly extending cutting edge lie on the same plane.

5. A bone drill according to claim 1 further including a first helical flute extending from said stabilizing point first flute and a first helical thread and a second helical flute extending from said stabilizing point second flute and a second helical thread.

6. A bone drill according to claim 5 wherein the orientation of said stabilizing point and said first and second lands is such as to cause bone chips generated by said first and second cutting edges to flow at an angle relative to said axis and bone chips generated by said first and second radially extending cutting edges to flow substantially parallel to said axis.

7. A bone drill according to claim 5 wherein each of said first and second helical threads includes a cylindrical wall section.

8. A bone drill according to claim 7 wherein said each of said first and second helical threads includes a concave arcuate section extending from one of said cylindrical wall sections to a helical flute.

9. A bone drill according to claim 8 wherein the intersection of one of said arcuate sections with said first helical thread defines a first end point and the intersection of the same arcuate section with a helical flute defines a second end point, a line extending through said first and second end points and through said axis being disposed at an angle of 20° to 40° relative to said axis.

10. A bone drill comprising:
   (a) an elongated shaft extending along an axis from a first end adapted to be engaged to a power means for rotating the shaft to a second end defining a tip lying substantially on said axis;
   (b) a stabilizing point extending from said tip toward said first end, said stabilizing point including
      (i) first and second wall sections extending from said tip tapering outwardly, at an acute angle relative to said axis in a direction toward said first end,
      (ii) a first cutting edge adjacent said first wall section and a second cutting edge adjacent said second wall section, and
      (iii) a first flute between said first cutting edge and said second wall section and a second flute between said second cutting edge and said first wall section; and
   (c) a first land extending substantially radially outwardly from said first wall section and a second land extending substantially radially outwardly from said second wall section, said first land including a first leading edge defining a cutting edge lying on a plane substantially perpendicular to said axis and said second land including a second leading edge defining a cutting edgy lying on a plane substantially perpendicular to said axis.

11. A bone drill according to claim 10 wherein a section taken along said axis and through said first wall section and said second wall section defines an angle between said first and second wall sections in the range of 60°±10°.

12. A bone drill according to claim 10 further including a first helical flute adjoining said first flute and a second helical flute adjoining said second flute said first and second helical flutes being separated by helical threads.

13. A bone drill according to claim 12 wherein each of said first and second helical threads includes a cylindrical wall section.

14. A bone drill according to claim 12 wherein said stabilizing point first and second flutes each define a contour which propels bone chips contacted thereby in a first direction at an angle relative to said axis and said first and second leading edges cooperate with said first and second helical flutes, respectively, to propel bone chips contacted thereby in a second direction different than said first direction.

15. A bone drill according to claim 14 wherein said second direction is generally parallel to said axis.

16. A bone drill according to claim 10 wherein said first leading edge is disposed 180° from said second leading edge.

17. A bone drill according to claim 10 wherein each said first cutting edge and said second cutting edge lie on a plane parallel to said axis.

18. A bone drill according to claim 17 wherein said first cutting edge and second cutting edge lie on the same plane.

19. A bone drill comprising:
   (a) an elongated shaft extending along an axis from a first end adapted to be engaged to a power means for rotating the shaft to a second end defining a tip lying substantially on said axis;
   (b) a stabilizing point extending from said tip toward said first end, said stabilizing point including
      (i) first and second wall sections extending from said tip tapering outwardly at an acute angle relative to said axis in a direction toward said first end,
      (ii) a first cutting edge adjacent said first wall section and a second cutting edge adjacent said second wall section,
      (iii) a first flute between said first cutting edge and said second wall section and a second flute between said second cutting edge and said first wall section; and
      (iv) a first helical flute adjoining said first flute and a second helical flute adjoining said second flute, said first and second helical flutes each being separated by helical threads, each of said first and second helical threads including a cylindrical wall section and a concave arcuate section extending from one of said cylindrical wall sections to a helical flute; and
   (c) a first land extending substantially radially outwardly from said first wall section and a second land extending substantially radially outwardly from said second wall section, said first land including a first leading edge defining a cutting edge and said second land including a second leading edge defining a cutting edge.

20. A bone drill according to claim 19 wherein the intersection of one of said arcuate sections with said first helical thread defines a first end point and the intersection of the same arcuate section with a helical flute defines a second end point, a line extending through said first and second end points and through said axis being disposed at an angle of 20° to 40° relative to said axis.

21. A bone drill comprising:
   (a) an elongated shaft extending along an axis from a first end adapted to be engaged to a power means for rotating the shaft to a second end defining a tip lying substantially on said axis;
   (b) a stabilizing point extending from said tip toward said first end, said stabilizing point including
      (i) first and second wall sections extending from said tip tapering outwardly at an acute angle relative to said axis in a direction toward said first end,
      (ii) a first cutting edge adjacent said first wall section and a second cutting edge adjacent said second wall section, said first cutting edge and said first leading edge lying on the same place, which plane is parallel to said axis, and
      (iii) a first flute between said first cutting edge and said second wall section and a second flute between said second cutting edge and said first wall section; and
   (c) a first land extending substantially radially outwardly from said first wall section and a second land extending substantially radially outwardly from said second wall section, said first land including a first leading edge defining a cutting edge and said second land including a second leading edge defining a cutting edge.

22. A bone drill according to claim 21 wherein said second cutting edge and said second leading edge lie on the same plane, which plane is parallel to said axis.

23. A bone drill comprising:
   (a) an elongated shaft extending along an axis from a first end adapted to be engaged to a power means for rotating the shaft to a second end defining a tip lying substantially on said axis;
   (b) a stabilized point extending from said tip toward said first end, said stabilizing point including
      (i) first and second wall sections extending from said tip tapering outwardly in a direction toward said first end, a section taken along said axis and through said first wall section and said second wall sections defining an angle between said first and second wall sections in the range of 60°±10°, (ii) a first cutting edge adjacent said first wall section and a second cutting edge adjacent said second wall section, and (iii) a first flute between said first cutting edge and said second wall section and a second flute between said second cutting edge and said first wall section;

(c) a first land extending substantially radially outwardly from said first wall section and a second land extending substantially radially outwardly from said second wall section, said first land including a first leading edge defining a cutting edge lying on the same plane as said first cutting edge, said plane being substantially perpendicular to said axis and said second land including a second leading edge defining a cutting edge lying on the same plane as said second cutting edge, said plane being substantially perpendicular to said axis, said first leading edge being disposed 180° from said second leading edge, and (d) a first helical flute adjoining said first flute and a second helical flute adjoining said second flute said first and second helical flutes being separated by helical threads.

24. A bone drill according to claim 23 wherein said stabilizing point first and second flutes each define a contour which propels bone chips contacted thereby in a first direction at an angle relative to said axis and said first and second leading edges cooperate with said first and second helical flutes, respectively, to propel bone chips contacted thereby in a second direction different than said first direction.

25. A bone drill according to claim 24 wherein said second direction is generally parallel to said axis.

* * * * *